United States Patent
Kim et al.

(10) Patent No.: US 12,264,125 B2
(45) Date of Patent: Apr. 1, 2025

(54) METHOD OF REMOVING METAL SUBSTANCE IN PETROCHEMICAL PRODUCT

(71) Applicant: LG CHEM, LTD., Seoul (KR)

(72) Inventors: Tae Woo Kim, Daejeon (KR); Sung Kyu Lee, Daejeon (KR); Byung Woo Choi, Daejeon (KR); Hong Soo Joo, Daejeon (KR); Dong Ha Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 163 days.

(21) Appl. No.: 17/765,432

(22) PCT Filed: Aug. 12, 2021

(86) PCT No.: PCT/KR2021/010713
§ 371 (c)(1),
(2) Date: Mar. 30, 2022

(87) PCT Pub. No.: WO2022/097885
PCT Pub. Date: May 12, 2022

(65) Prior Publication Data
US 2024/0109828 A1     Apr. 4, 2024

(30) Foreign Application Priority Data

Nov. 9, 2020     (KR) .......................... 10-2020-0148768

(51) Int. Cl.
*C07C 29/76*     (2006.01)
*B01D 15/36*     (2006.01)
(Continued)

(52) U.S. Cl.
CPC ............ *C07C 29/76* (2013.01); *B01D 15/361* (2013.01); *B01F 25/431* (2022.01); *B03C 1/286* (2013.01);
(Continued)

(58) Field of Classification Search
CPC .............................. C07C 29/76; C10G 53/08
See application file for complete search history.

(56) References Cited

U.S. PATENT DOCUMENTS

| | | | | |
|---|---|---|---|---|
| 5,607,575 A | * | 3/1997 | Kamiya | .................. C10G 32/02 209/214 |
| 2011/0186523 A1 | * | 8/2011 | Williamson | .......... B03C 1/0332 210/695 |
| 2019/0270939 A1 | | 9/2019 | Javeed et al. | |

FOREIGN PATENT DOCUMENTS

| | | |
|---|---|---|
| CN | 102597175 A | 7/2012 |
| CN | 207429831 U | 6/2018 |

(Continued)

*Primary Examiner* — Medhanit W Bahta
(74) *Attorney, Agent, or Firm* — Bryan Cave Leighton Paisner LLP

(57) ABSTRACT

A method of removing a metal substance in a petrochemical product including: supplying a petrochemical product stream to an incoming tank through a supply pipe, circulating the petrochemical product stream through an incoming tank circulation pipe, and removing a metal substance included in the petrochemical product stream using a magnetic filter; transporting the petrochemical product stream to an outgoing tank through an incoming tank discharge pipe which is branched from the incoming tank circulation pipe and connected to an outgoing tank; circulating the petrochemical product stream through an outgoing tank circulation pipe provided in the outgoing tank and removing the metal substance included in the petrochemical product stream using a magnetic filter; and transporting the petrochemical product stream to a branch pipe branched from the outgoing tank circulation pipe to remove the metal substance using an ion exchange resin filter.

11 Claims, 6 Drawing Sheets

(51) Int. Cl.
*B01F 25/431* (2022.01)
*B03C 1/28* (2006.01)
*C10G 25/02* (2006.01)
*C10G 32/02* (2006.01)
*C10G 53/02* (2006.01)
*C10G 53/08* (2006.01)
*B01F 25/00* (2022.01)

(52) U.S. Cl.
CPC .............. *C10G 25/02* (2013.01); *C10G 32/02* (2013.01); *C10G 53/08* (2013.01); *B01F 2025/913* (2022.01); *B03C 2201/18* (2013.01); *C10G 2300/205* (2013.01)

(56) References Cited

FOREIGN PATENT DOCUMENTS

| | | |
|---|---|---|
| CN | 105776491 B | 10/2018 |
| CN | 209412006 U | 9/2019 |
| JP | H06-100615 A | 4/1994 |
| JP | 2004-217800 A | 8/2004 |
| JP | 2005-120175 A | 5/2005 |
| KR | 10-2000-0005631 A | 1/2000 |
| KR | 10-2007-0018924 A | 2/2007 |
| KR | 10-2008-0113228 A | 12/2008 |
| KR | 10-2012-0083549 A | 7/2012 |
| KR | 10-2013-0000194 A | 1/2013 |
| KR | 10-2014-0125433 A | 10/2014 |
| KR | 10-2014-0130036 A | 11/2014 |
| KR | 2018-0051816 A | 5/2018 |
| KR | 2020-0036361 A | 4/2020 |

\* cited by examiner

[FIG. 1]
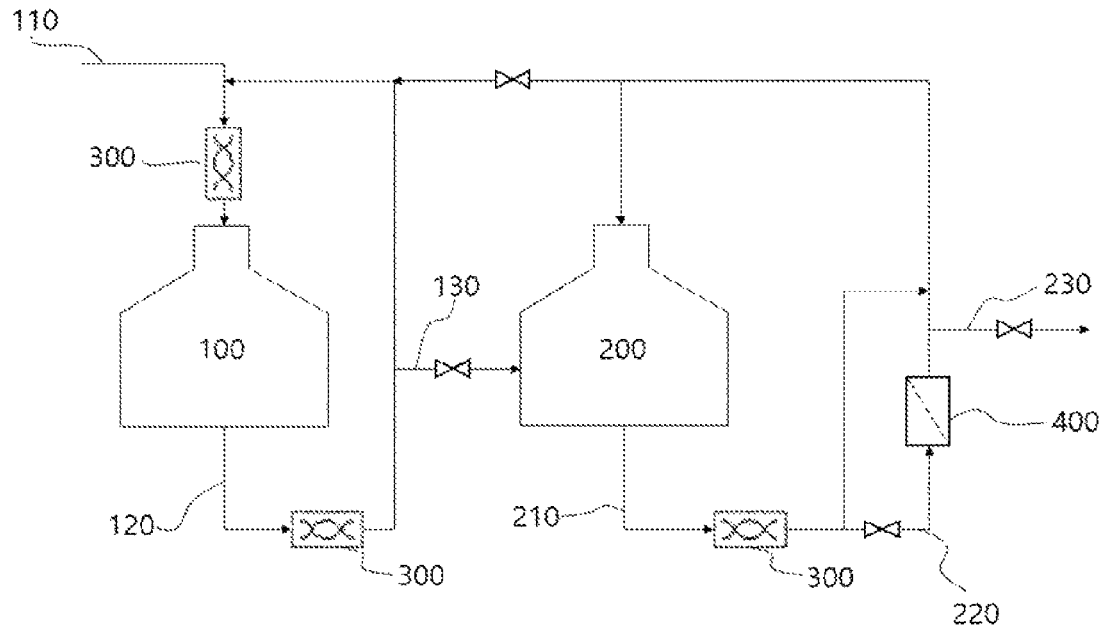
[FIG. 2]
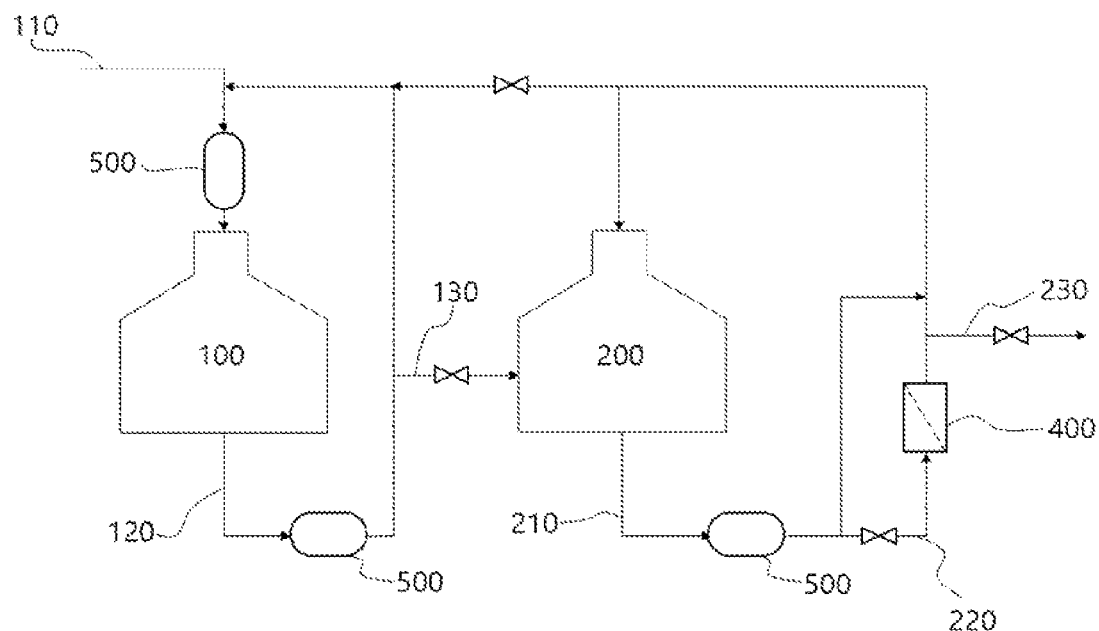

[FIG. 3]
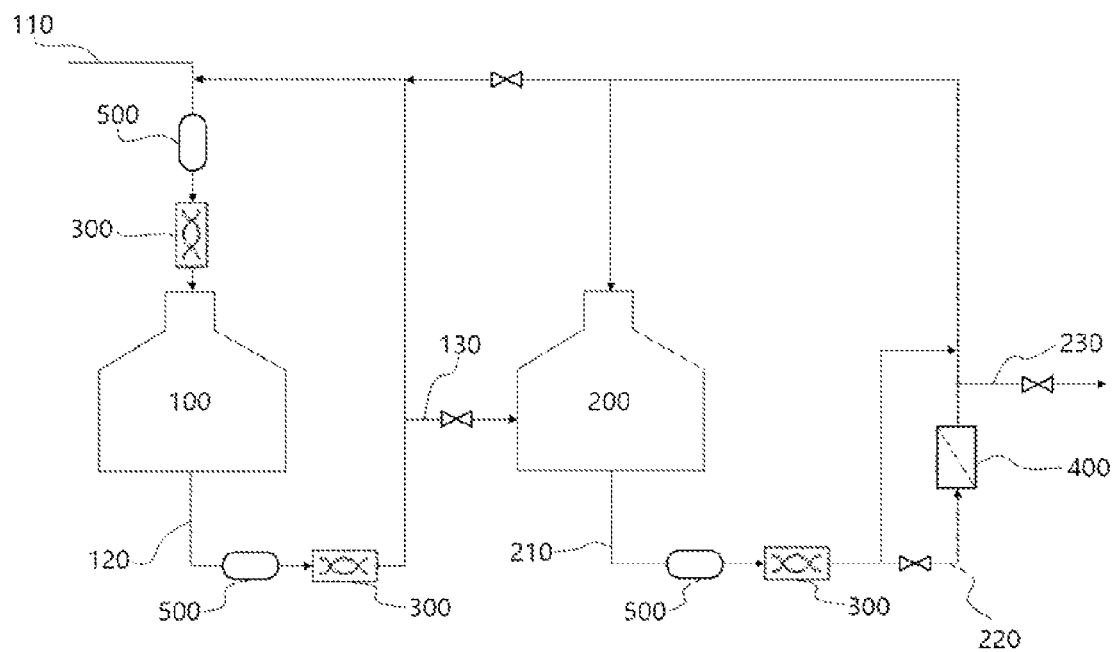
[FIG. 4]
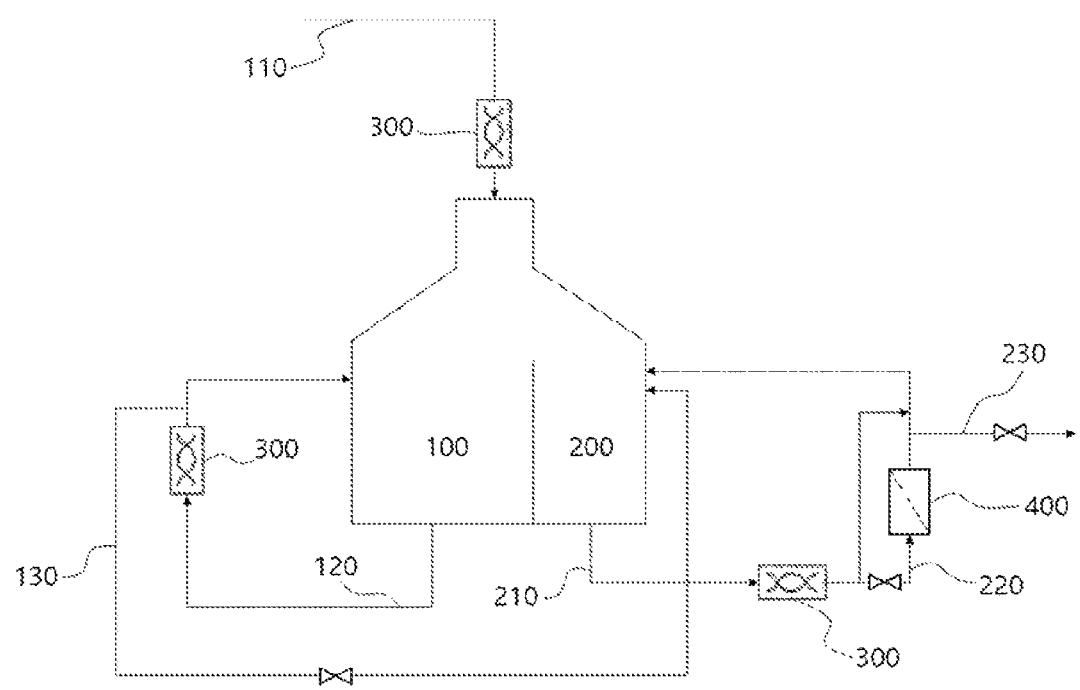

[FIG. 5]
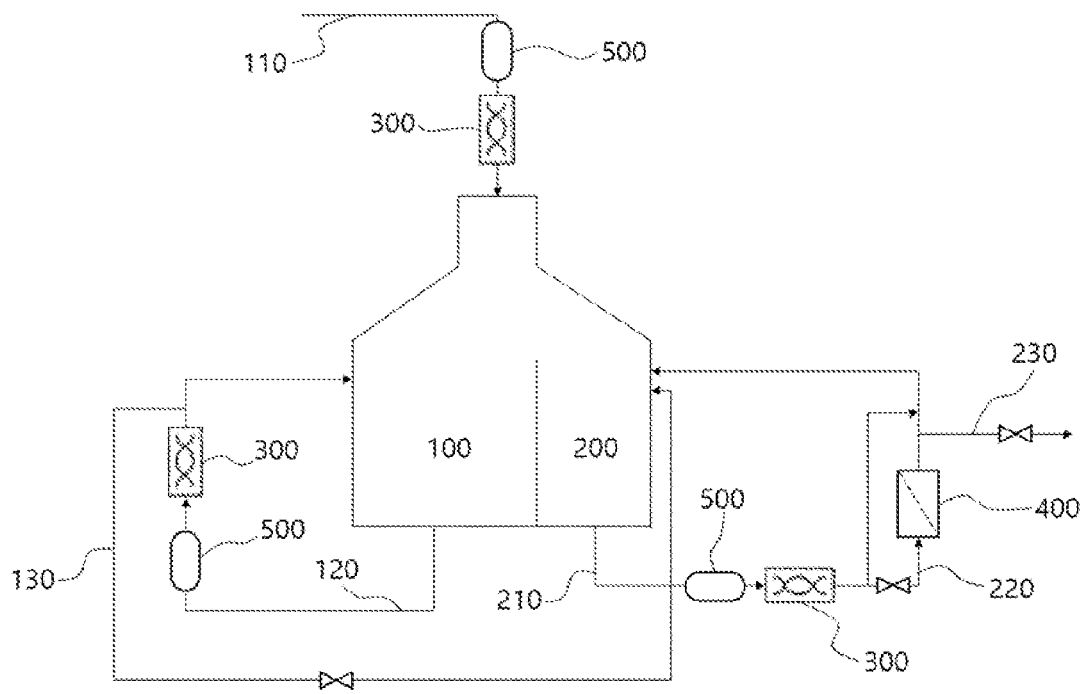
[FIG. 6]
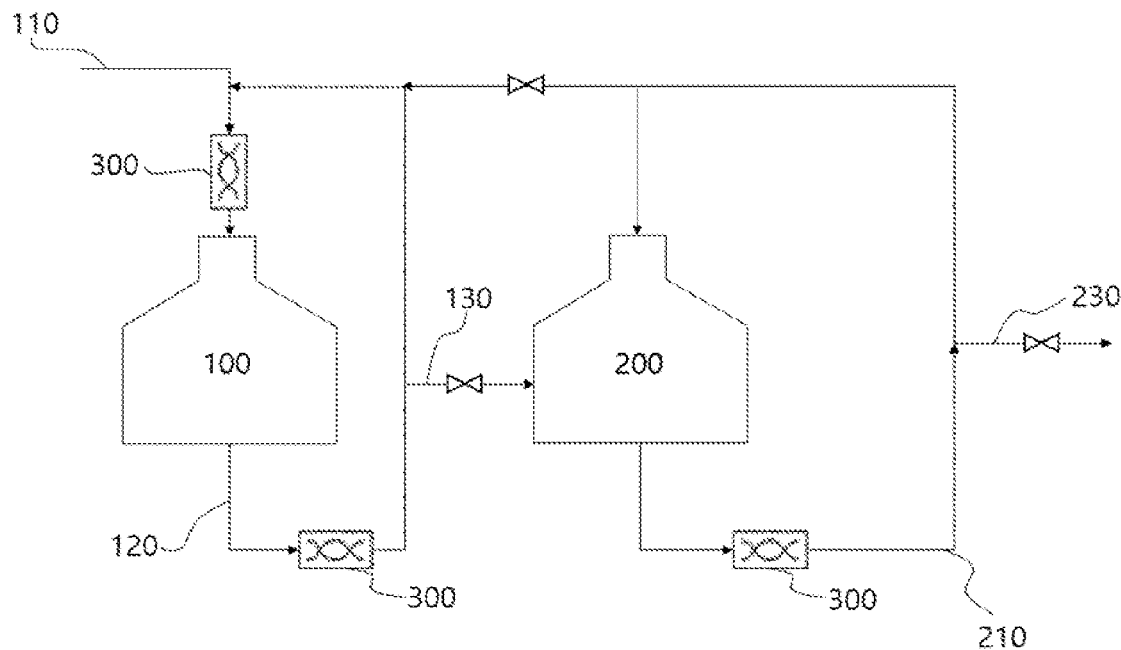

[FIG. 7]
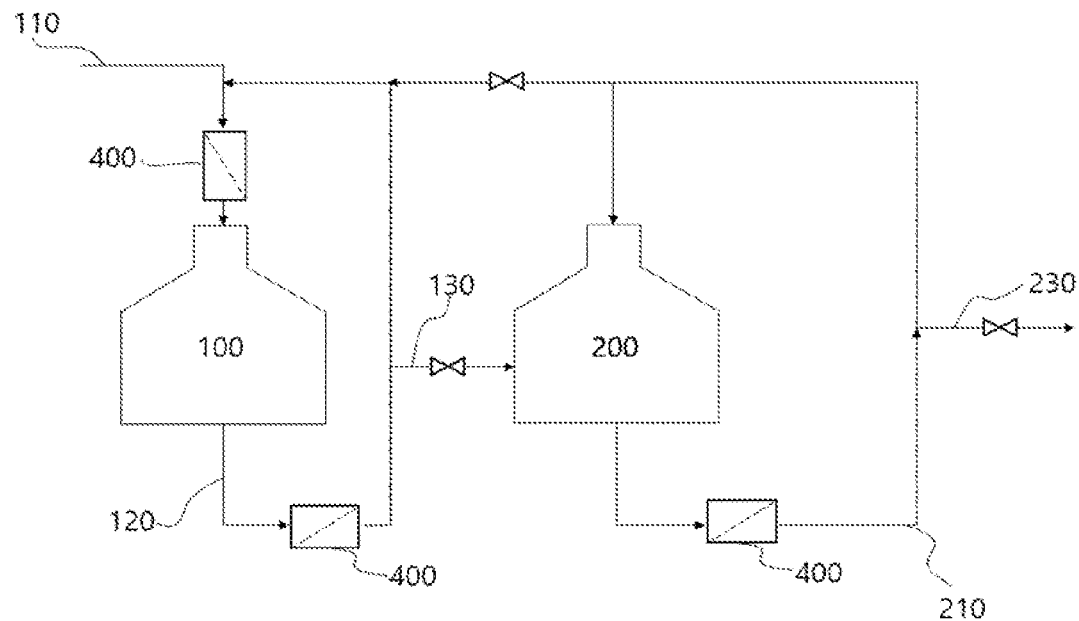
[FIG. 8]
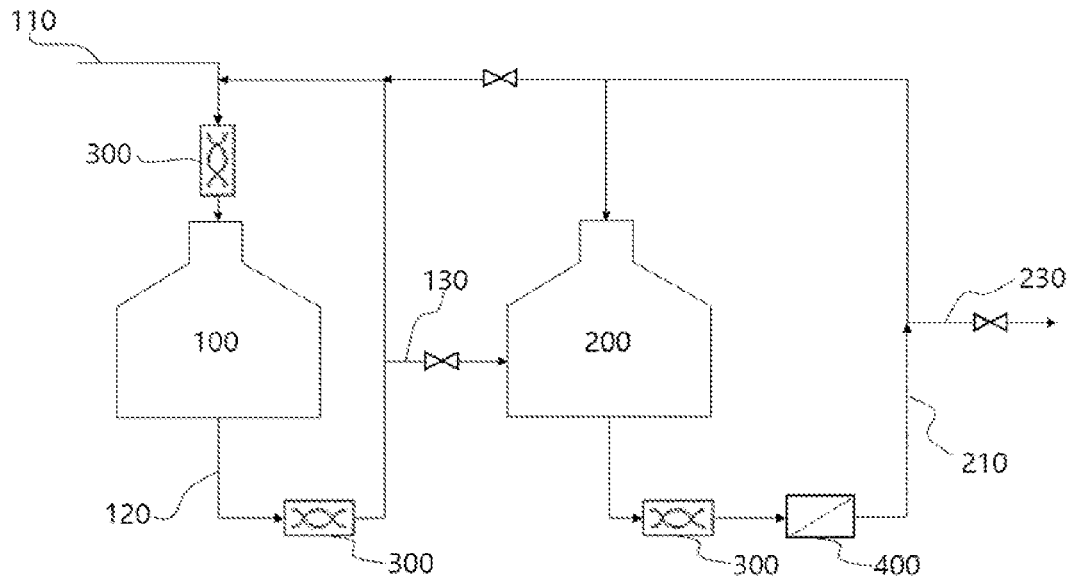

【FIG. 9】
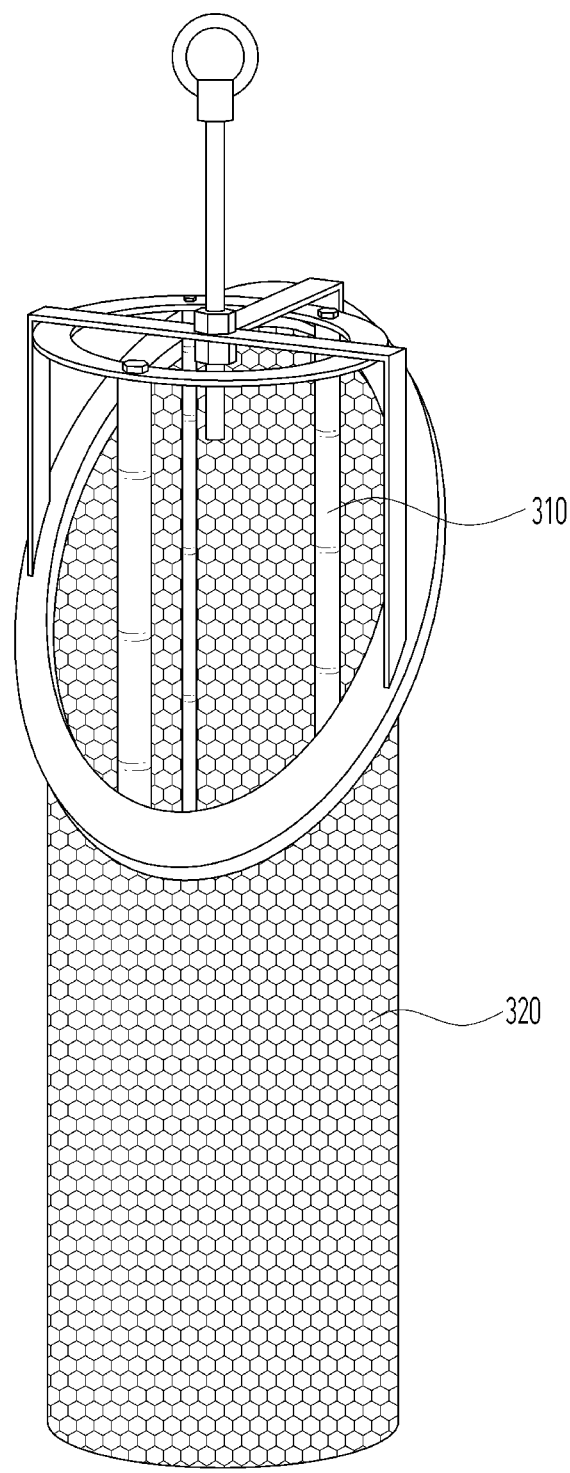

【FIG. 10A】
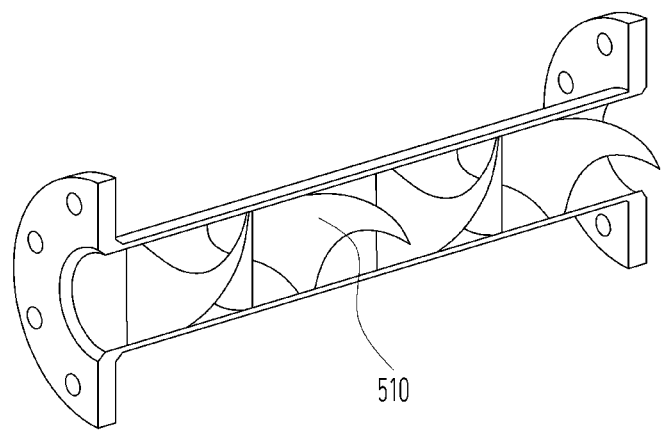
【FIG. 10B】
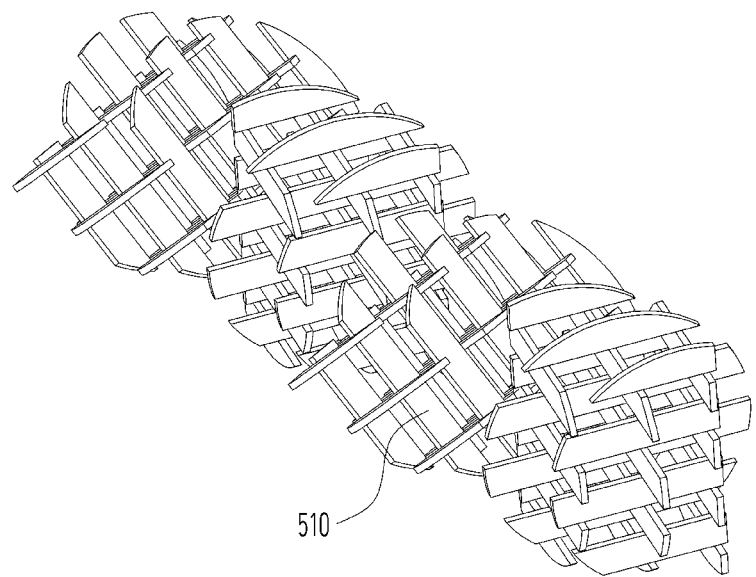

METHOD OF REMOVING METAL SUBSTANCE IN PETROCHEMICAL PRODUCT

CROSS-REFERENCE TO RELATED APPLICATIONS

This application is a US national phase of international application No. PCT/KR2021/010713, filed on Aug. 12, 2021, which claims the benefit of priority to Korean Patent Application No. 10-2020-0148768, filed on Nov. 9, 2020, the entire contents of which are incorporated as if fully set forth herein.

TECHNICAL FIELD

The present invention relates to a method of removing a metal substance in a petrochemical product, and more particularly, to a method of removing a metal substance included in a petrochemical product stream with low cost and high efficiency.

BACKGROUND

Some metal substances which corrode process equipment in a rear end process or are foreign matter affecting quality are included in a petrochemical product stream produced in a petrochemical process.

For example, when the petrochemical product isopropyl alcohol (IPA) is used as a solvent for cleaning semiconductors, metal substances included in the isopropyl alcohol may have a pernicious corrosive influence on semiconductors.

In addition, for a high-reactive monomer such as butadiene (BD), styrene monomers (SM), and acrylic acid (AA), the metal substance acts as a catalyst to derive an unintended reaction during storage or transport, so that the quality of the product may be deteriorated.

Thus, conventionally, a distillation method to remove the metal substance by boiling through distillation, a removal method using an ion exchange resin filter, and a removal method using a magnetic filter were mainly used as methods for removing a metal substance in the petrochemical product stream produced and discharged in a petrochemical process.

However, in the case of the distillation method, energy consumption is significantly increased, and additional devices need to be installed and operated, which increases device costs because all products undergo a vaporization process and then a liquefaction process.

In addition, for the method using an ion exchange resin filter, the ion exchange resin filter is significantly expensive, and in particular, when the method is used for removing a metal substance in a petrochemical product stream having a high metal content, very high maintenance costs are required.

In addition, for the method using a magnetic filter, the magnetic filter is inexpensive, but the effect of removing a metal substance is relatively low, so that it is difficult to secure sufficient metal substance removability.

Accordingly, there is currently a need to study a method for removing a metal substance in a petrochemical product stream with high efficiency at low cost.

SUMMARY

An objective of the present invention is to provide a method for removing a content of a metal substance in a petrochemical product at low cost with high efficiency and controlling the content easily to a desired level, in order to solve the problems discussed in the Background.

In one general aspect, a method of removing a metal substance in a petrochemical product includes: supplying a petrochemical product stream to an incoming tank through a supply pipe, circulating the stream through an incoming tank circulation pipe, and removing a metal substance included in the petrochemical product stream using one or more magnetic filters provided in any one or more of the supply pipe and the incoming tank circulation pipe; transporting the petrochemical product stream to an outgoing tank through an incoming tank discharge pipe which is branched from the incoming tank circulation pipe and connected to an outgoing tank; circulating the petrochemical product stream through an outgoing tank circulation pipe provided in the outgoing tank and removing the metal substance included in the petrochemical product stream using one or more magnetic filters provided in the outgoing tank circulation pipe; and transporting the petrochemical product stream to a branch pipe branched from the outgoing tank circulation pipe to remove the metal substance using one or more ion exchange resin filters provided in the branch pipe.

The method of removing a metal substance in a petrochemical product is designed so that the petrochemical product stream passes through an incoming tank and an outgoing tank sequentially, and a metal substance in the petrochemical product stream may be removed as much as possible at low cost using a magnetic filter in a circulation pipe of each of the incoming tank and the outgoing tank.

In addition, the present invention is provided with an ion exchange resin filter in a separation pipe branched from the outgoing tank circulation pipe, thereby allowing a content of the metal substance in the petrochemical product stream passing through the ion exchange resin filter to be controlled, and thus, excellent metal substance removability is secured and also maintenance costs of the ion exchange resin filter may be reduced.

In addition, the present invention includes an uneven portion that changes a fluid flow in the magnetic filter, thereby improving metal substance removability.

In addition, the present invention is provided with a static mixer in a front end of the magnetic filter, thereby improving metal substance removability of the magnetic filter.

BRIEF DESCRIPTION OF DRAWINGS

FIGS. 1 to 5 are process flow diagrams illustrating a method of removing a metal substance in a petrochemical product according to an exemplary embodiment of the present invention.

FIGS. 6 to 8 are process flow diagrams illustrating a method of removing a metal substance in a petrochemical product according to the Comparative Examples.

FIG. 9 is a photograph of a magnetic filter.

FIGS. 10A and 10B are photographs of a static mixer.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "upper portion" means a portion corresponding to a height at or above 50% of a total height of an apparatus in a container and the term "lower portion" means a portion corresponding to a height less than 50% of a total height of an apparatus in a container.

The term "stream" in the present invention may refer to a fluid flow in a process, or may refer to a fluid itself flowing in a pipe. Specifically, the stream may refer to both a fluid itself flowing in a pipe connecting each device and a fluid flow. In addition, the fluid may refer to a gas, a liquid, and the like. A case in which a solid substance is included in the fluid is not excluded.

Hereinafter, the present invention will be described in more detail, referring to FIGS. 1 to 5, 9, and 10, for better understanding of the present invention.

According to the present invention, a method of removing a metal substance in a petrochemical product is provided. More specifically, a method of removing a metal substance in a petrochemical product includes: supplying a petrochemical product stream to an incoming tank 100 through a supply pipe 110, circulating the stream through an incoming tank circulation pipe 120, and removing a metal substance included in the petrochemical product stream using one or more magnetic filters 300 provided in any one or more of the supply pipe 110 and the incoming tank circulation pipe 120; transporting the petrochemical product stream to an outgoing tank 200 through an incoming tank discharge pipe 130 which is branched from the incoming tank circulation pipe 120 and connected to an outgoing tank 200; circulating the petrochemical product stream through an outgoing tank circulation pipe 210 provided in the outgoing tank 200 and removing the metal substance included in the petrochemical product stream using one or more magnetic filters 300 provided in the outgoing tank circulation pipe 210; and transporting the petrochemical product stream to a branch pipe 220 branched from the outgoing tank circulation pipe 210 to remove the metal substance using one or more ion exchange resin filters 400 provided in the branch pipe 220.

Specifically, some metal substances which corrode process equipment in a rear end process or are foreign matter affecting quality are included in a petrochemical product stream produced in a petrochemical process. Here, the metal substance may include, for example, one or more selected from the group consisting of iron, nickel, molybdenum, and arsenic.

The petrochemical product stream is not particularly limited as long as it includes a product produced in a petrochemical process, and for example, the product may be isopropyl alcohol, butadiene, a styrene monomer, an acrylic acid stream, and the like.

The isopropyl alcohol (IPA) is a petrochemical product used as a solvent for cleaning semiconductors, and a metal substance included in the isopropyl alcohol may have a pernicious corrosive influence on semiconductors. In addition, in the case of a high-reactive monomer such as butadiene (BD), styrene monomers (SM), and acrylic acid (AA), the metal substance acts as a catalyst to derive an unintended reaction during storage or transport, which may deteriorate the quality of the product.

Conventionally, a distillation method to remove the metal substance by boiling through distillation, a removal method using an ion exchange resin filter 400, and a removal method using a magnetic filter 300 were mainly used.

However, when the distillation method is used, all products undergo a vaporization process and then a liquefaction process, thereby significantly increasing energy consumption and also additional devices need to be installed and operated, which increases device costs.

In addition, when the method using an ion exchange resin filter 400 is used, the ion exchange resin filter 400 is significantly expensive, and in particular, when the method is used for removing a metal substance in a petrochemical product stream having a high metal content, very high maintenance costs are required.

In addition, when the method using a magnetic filter 300 is used, the magnetic filter 300 is inexpensive, but the effect of removing a metal substance is relatively low, so that it is difficult to secure sufficient metal substance removability.

Thus, in the present invention, a process of removing a metal substance in a petrochemical product is designed so that removability of a metal substance using the inexpensive magnetic filter is improved and a use of the ion exchange resin filter 400 is minimized, and thus, a method of removing a metal substance in a petrochemical product with high efficiency at low cost is provided.

According to an exemplary embodiment of the present invention, a metal substance in the petrochemical product stream may be removed while a petrochemical product stream discharged from a petrochemical process is transported so as to pass through an incoming tank 100 and an outgoing tank 200 sequentially.

The incoming tank 100 and an outgoing tank 200 may be installed as a separate tank or may be formed as one tank with a partition therein. Specifically, when the incoming tank 100 and the outgoing tank 200 are installed as a separate tank, the size of each tank may be decreased, and even when tank repair is required, operation and product incoming and outgoing may be continued while the process is performed with one tank. In addition, when the incoming tank 100 and the outgoing tank 200 are formed as one tank with a partition therein, the installation cost of the tank may be saved and civil and plumbing works become simple, and thus, the metal substance in the petrochemical product may be removed by the method according to the present invention even in the case of a small factory area.

The petrochemical product stream may be supplied to an upper portion of the incoming tank 100 through a supply pipe 110. In addition, the petrochemical product stream is discharged to a lower portion of the incoming tank 100 through an incoming tank circulation pipe 120 from the incoming tank 100 and may be circulated to the incoming tank 100 again. For example, the incoming tank circulation pipe may be a pipe which is extended from the incoming tank 100 to join the supply pipe 110 or connected to the upper portion of the incoming tank 100 as a separate pipe.

Any one or more of the supply pipe 110 and the incoming tank circulation pipe 120 may be provided with one or more or one to three magnetic filters 300. Specifically, any one or more pipes of the supply pipe 110 to supply the petrochemical product stream to the incoming tank 100 and the incoming tank circulation pipe 120 to discharge the petrochemical product stream from the incoming tank 100 and circulate the stream to the incoming tank 100 again may be provided with one or more magnetic filters 300 to remove a metal substance in the petrochemical product stream. For example, one or more magnetic filters 300 may be provided in the incoming tank circulation pipe 120 or one or more magnetic filters 300 may be provided in each pipe of the supply pipe 110 and the incoming tank circulation pipe 120. As a more specific example, one magnetic filter 300 may be provided in the supply pipe 110 and one magnetic filter 300 may be provided in the incoming tank circulation pipe 120. In this case, the metal substance in the petrochemical product stream is primarily removed from the supply pipe 110 and the metal substance in the petrochemical product stream is continuously removed from the incoming tank circulation pipe 120, thereby effectively lowering a content of the metal substance included in the petrochemical product in the incoming tank 100. Here, the incoming tank circulation pipe may be joined to a front end of the magnetic filter 300 provided in the supply pipe 110 based on a flow direction of the petrochemical product stream and connected to the upper portion of the incoming tank 100.

According to an exemplary embodiment of the present invention, when the content of the metal substance included in the petrochemical product in the incoming tank 100 is decreased to a certain level, the petrochemical product stream may be transported to the outgoing tank 200 through an incoming tank discharge pipe 130 branched from the incoming tank circulation pipe 120 and connected to the outgoing tank 200.

The content of the metal substance content included in the petrochemical product when the petrochemical product stream is transported from the incoming tank 100 to the outgoing tank 200 may be properly adjusted depending on the kind of petrochemical product and a content level of the metal substance required in for a particular use. For example, when the content of the metal substance included in the petrochemical product in the incoming tank 100 is 100 ppb or less, 5 ppb to 100 ppb, or 7500 ppt to 8 ppb, the petrochemical product stream may be transported to the outgoing tank 200 through the incoming tank discharge pipe 130. As a more specific example, when the content of the metal substance included in the petrochemical product isopropyl alcohol in the incoming tank 100 is 8 ppb or less, 7 ppb to 8 ppb, or 6500 ppt to 7500 ppt, the isopropyl alcohol stream may be transported to the outgoing tank 200 through the incoming tank discharge pipe 130. In addition, when the content of the metal substance included in the petrochemical product, which may be a butadiene stream, a styrene monomer stream, or an acrylic acid stream, in the incoming tank 100 is 100 ppb or less, 50 ppb to 80 ppb, or ppb to 50 ppb, the butadiene stream, the styrene monomer stream, or the acrylic acid stream may be transported to the outgoing tank 200 through the incoming tank discharge pipe 130.

According to an exemplary embodiment of the present invention, the petrochemical product stream supplied from the incoming tank 100 to the outgoing tank 200 may be discharged from the outgoing tank 200 through an outgoing tank circulation pipe 210 extending from a lower portion of the outgoing tank 200 and connected to an upper portion of the outgoing tank 200, and recirculated to the outgoing tank 200.

The outgoing tank circulation pipe 210 may be provided with one or more magnetic filters 300. For example, one or more, one to three, or one or two magnetic filters 300 may be provided in the outgoing tank circulation pipe 210. As a more specific example, one magnetic filter 300 may be provided in the outgoing tank circulation pipe 210. In this case, the metal substance in the petrochemical product stream is continuously removed from the outgoing tank circulation pipe 210, thereby further lowering a content of the metal substance included in the petrochemical product in the outgoing tank 200.

According to an exemplary embodiment of the present invention, when the content of the metal substance included in the petrochemical product in the outgoing tank 200 is decreased to a certain level, the petrochemical product stream may be transported to a branch pipe 220 branched from the outgoing tank circulation pipe 210. Here, the branch pipe 220 may be provided with one or more, or one or two ion exchange resin filters 400. As such, a petrochemical product stream from which the metal substance is removed to a certain level or lower in the outgoing tank 200 is transported to the branch pipe 220 and most of the residual metal substance in the petrochemical product stream may be removed using the ion exchange resin filter 400.

The time when the petrochemical product stream is transported from the outgoing tank circulation pipe 210 to the branch pipe 220 may be properly adjusted depending on the kind of petrochemical product and a content level of the metal substance required in a used place. For example, when the content of the metal substance included in the petrochemical product in the outgoing tank 200 is 50 ppb or less, 5 ppb to 50 ppb, or 2 ppb to 5 ppb, the petrochemical product stream may be transported to the branch pipe 220. As a more specific example, when the content of the metal substance included in the petrochemical product, which may be an isopropyl alcohol stream, in the outgoing tank 200 is 3 ppb or less, 2 ppb to 3 ppb, or 2.3 ppb to 2.8 ppb, the isopropyl alcohol stream may be transported through the branch pipe 220. In addition, when the content of the metal substance included in the petrochemical product, which may be a butadiene stream, a styrene monomer stream, or an acrylic acid stream, in the outgoing tank 200 is 50 ppb or less, 40 ppb to 45 ppb, or 43 ppb to 50 ppb, the butadiene stream, the styrene monomer stream, or the acrylic acid stream may be transported to the outgoing tank 200 through the branch pipe 220.

Specifically, when the isopropyl alcohol is to be used as a solvent for cleaning semiconductors without semiconductor corrosion, the content of the metal substance is preferably 3 ppb or less, and in the case of butadiene, a styrene monomer, and an acrylic acid, the content of the metal substance is preferably 100 ppb or less for preventing a further reaction during storage or transport.

In this regard, in the present invention, a supply amount to each of the incoming tank 100 and the outgoing tank 200 of the petrochemical product stream, a circulation amount in each of the incoming tank 100 and the outgoing tank 200, and a transport amount to the branch pipe 220 are easily controlled, and the content of the metal substance may be controlled at low cost with high efficiency depending on the kind of petrochemical product and the content of the metal substance to be desired. Specifically, for the petrochemical product stream, the content of the metal substance is controlled using the magnetic filter 300 provided in the supply pipe 110, the incoming tank circulation pipe 120, and the outgoing tank circulation pipe 210, and only when the content of the metal substance is lowered to a desired range depending on the kind of the petrochemical product stream, the stream is transported to the branch pipe 220 and the residual metal substance is removed using the ion exchange resin filter 400. Thereby, improving the removability of the metal substance in the petrochemical product and also greatly increasing a lifetime of the expensive ion exchange resin filter 400.

According to an exemplary embodiment of the present invention, a step of joining the petrochemical product stream which has passed through the ion exchange resin filter 400 in the branch pipe 220 to the outgoing tank circulation pipe 210, and then circulating the stream to the outgoing tank 200 or discharging the stream through a release pipe 230 branched from the outgoing tank circulation pipe 210 may be further included.

Specifically, when the content of the metal substance included in the petrochemical product stream which has passed through the ion exchange resin filter 400 in the branch pipe 220 does not reach a desired level, the stream may join the outgoing tank circulation pipe 210 and then be circulated to the outgoing tank 200. However, when the content of the metal substance included in the petrochemical product stream which has passed through the ion exchange resin filter 400 in the branch pipe 220 reaches a desired level, the stream may be discharged through the release pipe 230 branched from the outgoing tank circulation pipe 210 and productized. As a specific example, after the metal substance is removed from the stream to a desired level using the magnetic filter 300 in the outgoing tank circulation pipe 210, the stream is transported to the branch pipe 220 to reach a desired content of the metal substance through the ion exchange resin filter 400, and then may be discharged through the release pipe 230 branched from the outgoing tank circulation pipe 210. In this case, further circulation is performed in the outgoing tank 200 to reduce the use of the ion exchange resin filter 400, and thus, the use of the ion exchange resin filter 400 is minimized to extend a change period of the ion exchange resin filter 400 having a replacement cost of about 50 million to 100 million KRW per one use, thereby reducing maintenance costs.

According to an exemplary embodiment of the present invention, a part of the petrochemical product stream circulated through the outgoing tank circulation pipe 210 may be transported to the incoming tank circulation pipe 120 for lowering the content of the metal substance included in the petrochemical product in the outgoing tank 200.

According to an exemplary embodiment of the present invention, the magnetic filter may include a magnetic unit 310 and a housing unit 320 in a mesh net housing the magnetic unit 310. Specifically, the magnetic filter 300 is installed in the pipe, the magnetic unit 310 is disposed in a flow direction of the petrochemical product stream in the pipe, and the housing unit surrounds the front end of the magnetic unit 310 based on a flow direction of the petrochemical product stream. In this case, the metal substance included in the petrochemical product stream is preliminarily filtered through the housing unit 320 in a mesh net form before being removed by being attached to the magnetic unit 310, a fluid flow is stopped to improve metal substance removability of the magnetic filter 300, and when an amount of the metal substance attached to the magnetic unit 310 of the magnetic filter 300 is increased, the magnetic filter 300 is dismantled and then washing is performed to extend a wash cycle to remove the metal substance.

According to an exemplary embodiment of the present invention, the magnetic unit 310 may include a plurality of magnetic bars disposed at regular intervals based on a pipe section. For example, the magnetic bar may have a circular rod shape made of stainless steel having a major axis in a length direction of the pipe and a minor axis in a diameter direction of the pipe.

The magnetic unit 310 may include, for example, 1 to 10, 2 to 6, or 2 to 4 magnetic bars. In this case, a contact area between the petrochemical product stream transported into the pipe and the magnetic bar may be increased to improve metal substance removability using the magnetic filter 300.

According to an exemplary embodiment of the present invention, the magnetic unit 310 may include an uneven portion that changes a fluid flow. Specifically, the shape of the uneven portion is not particularly limited as long as the shape affects the fluid flow. Since the magnetic unit 310 includes the uneven portion to increase the surface area of the magnetic unit 310, the contact area with the petrochemical product stream is increased, and a vortex flow is formed by changing the fluid flow to increase a contact frequency between the fluid and the magnetic unit, thereby improving metal substance removability of the magnetic filter 300.

The magnetic unit 310 may include a plurality of magnetic bars having an uneven portion, or use a static mixer 500 manufactured from a magnetic material.

The static mixer 500 is a mixing agitator provided with an element having a structure that changes a fluid flow and acts as the uneven portion 510 in the body, as shown in FIGS. 10A and 10B. Specifically, the petrochemical product stream transported to the pipe continuously passes through the element of the static mixer 500 to form a vortex flow.

To use the static mixer 500 as the magnetic unit 310, the static mixer 500 may be manufactured from a magnetic material. For example, the static mixer 500 may be manufactured using one or more magnetic materials selected from the group consisting of neodymium, ferrite, and Al—Ni—Co.

As such, the static mixer 500 may improve the attachment and removal of the metal substance on the surface of the static mixer manufactured from a magnetic material, as well as increase a contact area with the petrochemical product stream due to the morphological feature, thereby improving the metal substance removability.

According to an exemplary embodiment of the present invention, the front end of the magnetic filter 300 may further include the static mixer 500 based on a flow direction of the petrochemical product stream. Specifically, the static mixer 500 may be installed and fixed in the pipe at the front end of the magnetic filter 300 based on a flow direction of the petrochemical product stream, and thus, the petrochemical product stream may cause a vortex flow before passing through the magnetic filter 300 to improve the metal substance removability of the magnetic filter 300.

The static mixer 500 provided at the front end of the magnetic filter 300 includes an uneven portion 510 that changes a fluid flow, and the uneven portion 510 may form a vortex flow of the petrochemical product stream transported in the direction of the magnetic filter 300. Specifically, the static mixer 500 is a mixing agitator provided with an element having the uneven portion 510 in the body that changes a fluid flow, and may adopt a shape so that the flow of the petrochemical product stream changed by the element is guided in the direction of the magnetic unit 310 of the magnetic filter 300. For example, when the magnetic unit 310 includes a plurality of magnetic bars disposed at regular intervals based on a pipe section, the shape of the element may be such that the flow of the petrochemical product stream flows toward a plurality of magnetic bars when changed by the element. In this case, the contact between the magnetic unit 310 and the petrochemical product stream may be increased to further improve the metal substance removability of the magnetic filter 300.

According to an exemplary embodiment of the present invention, the kind of ion exchange resin filter 400 is not particularly limited as long as the metal substance may be removed. For example, an ion exchange resin filter 400 including one or more selected from the group consisting of $SO_4^{2-}$, $Cl^-·HCO_3^-$, and $SiO_2$ may be used.

Hereinabove, the method of removing a metal substance in a petrochemical product according to the present invention has been described and illustrated in the drawings, but the description and the illustration in the drawings are the description and the illustration of only core constitutions for understanding of the present invention, and in addition to the process and devices described above and illustrated in the drawings, the process and the devices which are not described and illustrated separately may be appropriately applied and used for carrying out the method of removing a metal substance in a petrochemical product according to the present invention.

Hereinafter, the present invention will be described in more detail by the Examples. However, the following Examples are provided for illustrating the present invention, and it is apparent to a person skilled in the art that various modifications and alterations may be made without departing from the scope and spirit of the present invention and the scope of the present invention is not limited thereto.

EXAMPLES

Example 1

As illustrated in FIG. 1, a metal substance included in an isopropyl alcohol stream produced in a petrochemical process was removed.

Specifically, a metal substance was partially removed from the isopropyl alcohol stream via a magnetic filter 300 through a supply pipe 110, and then the stream was supplied to an incoming tank 100. In the incoming tank 100, the metal substance was further removed while circulating the isopropyl alcohol stream through an incoming tank circulation pipe 120 provided with the magnetic filter 300.

When the content of the metal substance included in isopropyl alcohol in the incoming tank 100 was decreased to 8 ppb or less, the petrochemical product stream was transported to an outgoing tank 200 through an incoming tank discharge pipe 130 branched from the incoming tank circulation pipe 120 and connected to the outgoing tank 200.

The metal substance was further removed while circulating the isopropyl alcohol stream through an outgoing tank circulation pipe 210.

When the content of the metal substance included in isopropyl alcohol in the outgoing tank 200 was decreased to ppb or less, the isopropyl alcohol stream was transported to a branch pipe 220 branched from the outgoing tank circulation pipe 210, the residual metal substance was removed using an ion exchange resin filter 400 provided in the branch pipe 220 and then the content of the metal substance was decreased to 3 ppb or less, and the stream was discharged through a release pipe 230 branched from the outgoing tank circulation pipe 210 and productized.

In this example, the magnetic filter 300 included a magnetic unit 310 including three magnetic bars and a housing unit 320, as shown in FIG. 9.

As a result, the content of the metal substance included in isopropyl alcohol was lowered to 3 ppb or less in 4 hours after the start of operation. In addition, it was confirmed that the replacement cycle of the ion exchange resin filter 400 was extended to 3 months or more.

Example 2

As illustrated in FIG. 2, a metal substance included in an isopropyl alcohol stream produced in a petrochemical process was removed.

Specifically, the metal substance included in the isopropyl alcohol stream was removed in the same manner as in Example 1, except that a static mixer 500 as shown in FIG. 10A, and manufactured from a neodymium material, was used as the magnetic filter 300 of Example 1.

As a result, the content of the metal substance included in isopropyl alcohol was lowered to 3 ppb or less in 4 hours after the start of operation. In addition, it was confirmed that the replacement cycle of the ion exchange resin filter 400 was extended to 12 months or more.

Example 3

As illustrated in FIG. 3, a metal substance included in an isopropyl alcohol stream produced in a petrochemical process was removed.

Specifically, the metal substance included in the isopropyl alcohol stream was removed in the same manner as in Example 1, except that a static mixer 500 as shown in FIG. 10A was provided at the front end of the magnetic filter 300 of Example 1.

As a result, the content of the metal substance included in isopropyl alcohol was lowered to 3 ppb or less in 4 hours after the start of operation. In addition, it was confirmed that the replacement cycle of the ion exchange resin filter 400 was extended to 8 months or more.

Example 4

As illustrated in FIG. 4, a metal substance included in an isopropyl alcohol stream produced in a petrochemical process was removed.

Specifically, the metal substance included in the isopropyl alcohol stream was removed in the same manner as in Example 1, except that one tank was used that included both the incoming tank 100 and the outgoing tank 200 separated with a partition.

As a result, the content of the metal substance included in isopropyl alcohol was lowered to 3 ppb or less in 4 hours after the start of operation. In addition, it was confirmed that the replacement cycle of the ion exchange resin filter 400 was extended to 3 months or more.

Example 5

As illustrated in FIG. 5, a metal substance included in an isopropyl alcohol stream produced in a petrochemical process was removed.

Specifically, the metal substance included in the isopropyl alcohol stream was removed in the same manner as in Example 4, except that a static mixer 500 as shown in FIG. 10A was provided at the front end of the magnetic filter 300 of Example 4.

As a result, the content of the metal substance included in isopropyl alcohol was lowered to 3 ppb or less in 4 hours after the start of operation. In addition, it was confirmed that the replacement cycle of the ion exchange resin filter 400 was extended to 8 months or more.

COMPARATIVE EXAMPLES

Comparative Example 1

As illustrated in FIG. 6, a metal substance included in an isopropyl alcohol stream produced in a petrochemical process was removed.

Specifically, a metal substance was partially removed from the isopropyl alcohol stream via a magnetic filter 300 through a supply pipe 110, and then the stream was supplied to an incoming tank 100. In the incoming tank 100, the metal substance was further removed while circulating the isopropyl alcohol stream through an incoming tank circulation pipe 120 provided with the magnetic filter 300.

When the content of the metal substance included in isopropyl alcohol in the incoming tank 100 was decreased to 8 ppb or less, the petrochemical product stream was transported to an outgoing tank 200 through an incoming tank discharge pipe 130 branched from the incoming tank circulation pipe 120 and connected to the outgoing tank 200.

The metal substance was further removed using the magnetic filter 300 while circulating the isopropyl alcohol stream through the outgoing tank circulation pipe 210, thereby lowering the content of the metal substance to 5 ppb or less, and the isopropyl alcohol stream was discharged through the release pipe 230 branched from the outgoing tank circulation pipe 210 to be provided and productized.

In this Comparative Example, the magnetic filter 300 included a magnetic unit 310 including three magnetic bars and a housing unit 320, as shown in FIG. 9.

As a result, it was confirmed that even with the operation for 24 hours, which is longer than in Example 1, the content of the metal substance in the petrochemical product stream was only decreased to a level of 4 ppb to 5 ppb using the magnetic filter 300 alone.

Comparative Example 2

As illustrated in FIG. 7, a metal substance included in an isopropyl alcohol stream produced in a petrochemical process was removed.

Specifically, a metal substance was partially removed from the isopropyl alcohol stream via an ion exchange resin filter 400 through a supply pipe 110, and then the stream was supplied to an incoming tank 100. In the incoming tank 100, the metal substance was further removed while circulating the isopropyl alcohol stream through an incoming tank circulation pipe 120 provided with the ion exchange resin filter 400.

When the content of the metal substance included in isopropyl alcohol in the incoming tank 100 was decreased to 8 ppb or less, the petrochemical product stream was transported to an outgoing tank 200 through an incoming tank discharge pipe 130 branched from the incoming tank circulation pipe 120 and connected to the outgoing tank 200.

The metal substance was further removed using the ion exchange resin filter 400 while circulating the isopropyl alcohol stream through the outgoing tank circulation pipe 210, thereby lowering the content of the metal substance to 3 ppb or less, and the isopropyl alcohol stream was discharged through the release pipe 230 branched from the outgoing tank circulation pipe 210 to be provided and productized.

As a result, the metal substance removability was equivalent to those of the Examples, but due to a low metal substance removal capacity of the ion exchange resin filter 400, the filter needs to be replaced every about 15 days, which is not preferred in terms of time and costs, and the cost of isopropyl alcohol was increased.

Comparative Example 3

As illustrated in FIG. 8, a metal substance included in an isopropyl alcohol stream produced in a petrochemical process was removed.

Specifically, a metal substance was partially removed from the isopropyl alcohol stream via a magnetic filter 300 through a supply pipe 110, and then the stream was supplied to an incoming tank 100. In the incoming tank 100, the metal substance was further removed while circulating the isopropyl alcohol stream through an incoming tank circulation pipe 120 provided with the magnetic filter 300.

When the content of the metal substance included in isopropyl alcohol in the incoming tank 100 was decreased to 8 ppb or less, the petrochemical product stream was transported to an outgoing tank 200 through an incoming tank discharge pipe 130 branched from the incoming tank circulation pipe 120 and connected to the outgoing tank 200.

The metal substance was further removed using the magnetic filter 300 and the ion exchange resin filter 400 while circulating the isopropyl alcohol stream through the outgoing tank circulation pipe 210, thereby lowering the content of the metal substance to 3 ppb or less, and the isopropyl alcohol stream was discharged through the release pipe 230 branched from the outgoing tank circulation pipe 210 to be provided and productized.

In this Comparative Example, the magnetic filter 300 included a magnetic unit 310 including three magnetic bars and a housing unit 320, as shown in FIG. 9.

As a result, the metal substance removability was equivalent to those of the Examples, but since a total amount of the isopropyl alcohol stream circulated to the outgoing tank 200 was circulated to the ion exchange resin filter 400, the replacement cycle of the ion exchange resin filter 400 was about 1 month. Thus, it was difficult to achieve the extension effect of the ion exchange resin filter 400 similar to the Examples, which is thus not preferred in terms of time and costs, and the cost of isopropyl alcohol was increased.

The invention claimed is:

1. A method of removing a metal substance in a petrochemical product, the method comprising:
   supplying a petrochemical product stream to an incoming tank through a supply pipe, circulating the petrochemical product stream through an incoming tank circulation pipe, and removing a metal substance included in the petrochemical product stream using one or more first magnetic filters provided in any one or more of the supply pipe and the incoming tank circulation pipe;
   transporting the petrochemical product stream to an outgoing tank through an incoming tank discharge pipe which is branched from the incoming tank circulation pipe and connected to the outgoing tank;
   circulating the petrochemical product stream through an outgoing tank circulation pipe provided in the outgoing tank and removing the metal substance included in the petrochemical product stream using one or more second magnetic filters provided in the outgoing tank circulation pipe; and
   transporting the petrochemical product stream to a branch pipe branched from the outgoing tank circulation pipe, wherein the branch pipe comprises one or more ion exchange resins filters to remove the metal substance.

2. The method of claim 1, further comprising: joining-feeding the petrochemical product stream which has passed through the ion exchange resin filter in the branch pipe to the outgoing tank circulation pipe, and then circulating the petrochemical product stream to the outgoing tank or discharging the petrochemical product stream through a release pipe branched from the outgoing tank circulation pipe.

3. The method of claim 1, wherein the magnetic filter includes:
   a magnetic unit; and
   a housing unit for the magnetic unit, wherein the housing unit comprises a mesh net.

4. The method of claim 3, wherein the magnetic unit includes a plurality of magnetic bars disposed at regular intervals in a pipe section.

5. The method of claim 3, wherein the magnetic unit includes an uneven portion changing that changes a fluid flow.

6. The method of claim 3, wherein the magnetic unit includes a static mixer manufactured from a magnetic material.

7. The method of claim 3, further comprising a static mixer, wherein the static mixer is positioned at a front end of the magnetic filter based on a flow direction of the petrochemical product stream.

8. The method of claim 7, wherein the static mixer includes an uneven portion that increases a vortex flow of the petrochemical product stream transported in a magnetic unit direction by changing a fluid flow.

9. The method of claim 1, wherein the petrochemical product stream is transported to the outgoing tank through the incoming tank discharge pipe when a content of the metal substance included in the petrochemical product stream in the incoming tank is 100 ppb or less.

10. The method of claim 1, wherein the petrochemical product stream is transported to the branch pipe when a content of the metal substance included in the petrochemical product stream in the outgoing tank is 50 ppb or less.

11. The method of claim 1, wherein the incoming tank and the outgoing tank are provided in a single tank comprising a partition.

\* \* \* \* \*